United States Patent [19]
Covey et al.

[11] Patent Number: 4,754,076
[45] Date of Patent: Jun. 28, 1988

[54] PROCESS FOR MAKING PHENOXYCYCLOALKANOLS

[75] Inventors: Rupert A. Covey, Bethany; Shih Y. Ma, Cheshire, both of Conn.

[73] Assignee: Uniroyal Chemical Company, Inc., Middlebury, Conn.

[21] Appl. No.: 831,040

[22] Filed: Feb. 19, 1986

Related U.S. Application Data

[63] Continuation-in-part of Ser. No. 583,452, Feb. 24, 1984, abandoned.

[51] Int. Cl.$^4$ ............................................. C07C 41/03
[52] U.S. Cl. ................................... 568/644; 568/606; 568/646; 568/670
[58] Field of Search ................ 568/644, 646, 606, 670

[56] References Cited

U.S. PATENT DOCUMENTS 2,213,477 9/1940 Steindorff et al. .............. 568/606 X
2,723,294 11/1955 Benoit ................................ 568/606
3,042,666 7/1962 Gentles ........................... 568/606 X
3,272,854 9/1966 Covey et al. .................... 568/644 X

OTHER PUBLICATIONS

Parker, Chem. Rev. 59 (1959) 737–763, 790–799.
Posner et al, Jour. Amer. Chem. Soc. 99 (1977) 8208, 8214–8218.
Rowton et al, J. Org. Chem. 23, 1057 (1958).

Primary Examiner—Howard T. Mars
Attorney, Agent, or Firm—William E. Dickheiser

[57] ABSTRACT

A process for producing a phenoxycycloalkanol comprising reacting an aromatic alcohol with an (optionally substituted) $C_5$–$C_6$ cycloalk-1,2-ylene oxide in the presence of an effective amount of a sodium-containing catalyst selected from the group consisting of sodium metal, $C_1$–$C_8$ sodium alkoxide, $C_6$–$C_{10}$ sodium aryloxide, $C_7$–$C_9$ sodium alkaryloxide and sodium hydride at between about 170° C. and about 225° C.

9 Claims, No Drawings

PROCESS FOR MAKING PHENOXYCYCLOALKANOLS

This application is a continuation-in-part of U.S. patent application Ser. No. 583,452, filed Feb. 24, 1984 now abandoned.

FIELD OF THE INVENTION

This invention is directed to an improved process for making phenoxycycloalkanols, which process comprises reacting an aromatic alcohol with an (optionally substituted) $C_5$-$C_6$cycloalkyl-1,2-ylene oxide in the presence of an effective amount of a specified sodium-containing catalyst at between about 170° C. and about 225° C. These phenoxycycloalkanols are useful intermediates in the production of cycloaliphatic sulfite ester pesticides and plasticizers.

BACKGROUND OF THE INVENTION

Cycloaliphatic sulfite esters have found wide acceptance as pesticides, particularly as miticides, and as plasticizers. A particularly valuable class of intermediates for the production of such ester compounds are phenoxycycloalkanols. Thus, Covey et al., in U.S. Pat. No. 3,272,854 show the use of phenoxycycloalkanols as intermediates in the production of cycloaliphatic sulfite esters.

Moreover, U.S. Pat. No. 3,272,854 further discloses a method of producing phenoxycycloalkanols, which method comprises reacting p-tert-butylphenol with cyclohexene oxide in the presence of 1 to 1.5% by weight, based on the weight of the p-tert-butylphenol, of sodium hydroxide. However, a difficulty associated with such sodium hydroxide catalyzed process is that a relatively large concentration of sodium hydroxide is required. This requirement imposes an economic penalty as well as necessitates neutralization of the product of the reaction with acid and removal of the water of neutralization formed thereby. Moreover, as is illustrated in the Examples below, the use of sodium hydroxide results in the production of comparatively large amounts of undesirable by-products.

Gentles, in U.S. Pat. No. 3,042,666 discloses a process for the manufacture of polyether derivatives comprising reacting polyhydroxylic compounds with alkylene oxides employing dimethylsulfoxide as a reaction medium and an alkaline catalyst, for example alkali metals and alkaline earth metals or hydroxides of such metals. This reaction is performed at a temperature between 50° C. and 150° C., preferably between 90° C. and 120° C.

Benoit, in U.S. Pat. No. 3,723,294, discloses a process for the copolymerization of an alcohol, preferably a monohydroxy aliphatic alcohol, and a mixture of alkene oxides containing propene oxide and pentene oxide. This process employs a catalyst which may be an alkali metal hydroxide or alkali metal alcoholate, and is conducted at temperatures between about 175° F. (about 80° C.) and 325° F. (about 163° C.), preferably at between about 210° F. (about 99° C.) and about 300° F. (about 149° C.).

U.S. Pat. No. 2,213,477 to Steindorff et al. discloses a process for producing polyglycol ethers of isocyclic hydroxyl compounds comprising reacting an alkylene glycol with a substituted isocyclic hydroxyl compound in the presence of a wide range of catalysts, including caustic alkalis, alkali alcoholates, tertiary organic bases and acid compounds (e.g. potassium bisulfate). It is noteworthy that the only example of this disclosure which employs a temperature in excess of 160° C. (Example 12) utilizes powdered caustic soda (i.e., NaOH) as a catalyst.

Rowton et al., J. Org. Chem. 23 1057 (1958) discloses the reaction of phenol with 1-bromo-2,3-epoxybutane and 3-bromo-1,2-epoxybutane to yield 3-phenoxy-1,2-epoxybutane and 1-phenoxy-2,3-epoxybutane, respectively.

Parker et al., Chem Rev. 59 737 (1959) is a review article discussing mechanisms of epoxide reactions. Although reactions employing cyclohexene oxide are mentioned, no reaction parameters are cited and none of the reactions involving this compound include the reaction of cyclohexene oxide with compounds having the formula ROH, where R is phenyl or a substituted phenyl.

Posner et al., JACS 99 8208 (1977) teaches the reaction of cycloalkene oxides with alumina in which allylic alcohols are the major product. Cyclohexene oxide is specifically indicated to be unusual in that the major product of its reaction with alumina is the trans 1,2-diol. No disclosure is included of reacting these epoxides with a compound of the formula ROH.

Posner et al, JACS 99, 8214 (1977), a related article, is directed to the same subject matter as the previously recited article. This article is further removed from the instant invention in that it is directed to the reaction of three epoxides: cyclopentadiene monooxide: 1,3-cyclohexadienemonooxide: and indene oxide, which are each acid-sensitive. These compounds are reacted with alumina to produce alcoholic products similar to those produced in the above discussed article.

While certain of the above-identified processes may be employed to produce phenoxycycloalkanols, such processes frequently have drawbacks including low efficiencies and the production of undesirable side-products, e.g. polyethers, associated with their use.

Accordingly, it is an object of this invention to provide a process for the production of phenoxycycloalkanols, which process produces increased yields of such compounds.

It is another object of this invention to provide a process for the production of phenoxycycloalkanols, which process results in reduced amounts of undesirable byproducts, such as polyethers, being produced.

The above and additional objects will become more fully apparent from the following description and accompanying Examples.

DESCRIPTION OF THE INVENTION

This invention relates to a process for producing a compound having the structure:

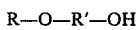

R—O—R'—OH wherein:
R is phenyl or phenyl substituted with one or more member of group consisting of:
  $C_1$-$C_4$ alkyl,
  $C_1$-$C_4$ alkoxy and methylene-dioxy; and
R' is $C_5$-$C_6$ cycloalk-1,2-ylene or $C_5$-$C_6$ cycloalk-1,2-ylene substituted with one or more member of the group consisting of:
  $C_1$-$C_4$ alkyl and
  $C_1$-$C_4$ alkoxy;
comprising reacting at between about 170° C. and about 225° C.:

(A) a compound having the formula ROH wherein R is as defined above; and
(B) at least one member of the group consisting of:
  cyclopentene oxide,
  cyclohexene oxide,
  cyclopentene oxide substituted with one or more member of the group consisting of $C_1$–$C_4$ alkyl, $C_1$–$C_4$ alkoxy and vinyl; and
  cyclohexene oxide substituted with one or more member selected from the group consisting of $C_1$–$C_4$ alkyl, $C_1$–$C_4$ alkoxy, and vinyl:
in the presence of an effective amount of sodium containing catalyst selected from the group consisting of sodium metal, $C_1$–$C_8$ sodium alkoxide, $C_6$–$C_{10}$ sodium aryloxide, $C_7$–$C_9$ sodium alkaryloxide and sodium hydride.

This invention relates to an improved process for the production of compounds having the formula R—O—R'—OH wherein R and R' are as described in formula I above. These compounds are useful intermediates in the production of organic sulfite esters useful as pesticides and plasticizers.

This process comprises reacting (A) an aromatic alcohol of the formula R-OH, wherein R is as defined above; and (B) a compound selected from the group consisting of cyclopentene oxide, cyclohexene oxide, or either of cyclopentene oxide or cyclohexene oxide substituted with $C_1$–$C_4$ alkyl, $C_1$–$C_4$ alkoxy or vinyl. Preferably, the molar ratio of reactant (A) to reactant (B) will be between about 5:4 and about 4:5, with stochiometric amounts of such compounds being particularly desired. However, the molar ratio of these compounds may be varied widely as desired.

The above-described reaction occurs in the presence of an effective amount of a sodium-containing catalyst selected from the group consisting of sodium metal, $C_1$–$C_8$ sodium alkoxide, sodium hydride, $C_6$–$C_{10}$ sodium aryloxide, or $C_7$–$C_9$ sodium alkaryloxide. Preferred catalysts include sodium metal, sodium methoxide, sodium ethoxide, sodium isopropoxide, sodium phenoxide, sodium para-tert-butylphenoxide and sodium p-tolueneoxide, with sodium metal, sodium methoxide and sodium para-tert-butylphenoxide being particularly preferred.

As employed herein, the term "an effective amount of a sodium-containing catalyst" refers to an amount of catalyst useful to produce product at the particular reaction parameters selected. This amount will vary in accordance with a number of factors, including the particular catalyst employed, the particular reactants selected, the reaction temperature selected and the like. However, one skilled in the art may readily determine by routine experimentation the amounts of a given catalyst which may be employed for any given set of reaction parameters. Generally, the amount of sodium catalyst necessary to effectively catalyze the reaction will range between about 0.01 and about 5% by weight, based on the weight of the (A) component, ROH. Typically, the amount of sodium containing catalyst preferably employed in the reaction is between about 0.05% and about 1% by weight, based on the weight of the (A) component, ROH.

The process of this invention is conducted at between about 170° C. and about 225° C., preferably between about 175° C. and about 210° C. As is indicated in the following Examples, such temperatures are important to obtain the increased yields afforded by the process of this invention.

Reaction time is not critical, and may range from several hours or more to several minutes or less depending on the particular reaction parameters selected.

The process of this invention is typically performed as follows. The reaction vessel is typically dried by sweeping with an inert gas, such as nitrogen. The sodium-containing catalyst and aromatic alcohol are introduced to the vessel. The vessel is heated to the desired reaction temperature and the cycloalkylene oxide component slowly added while the reaction mass is subjected to agitation. Upon completion of the addition of the cycloalkylene oxide, agitation and heat are continued until the reaction has progressed until the desired extent.

It is to be noted that the above-description is merely typical and may be varied widely, with the reaction components being added in any order. Moreover, by making adjustments well known to one skilled in the art the batch-type process described above may be accomplished in a continuous manner.

The process of this invention produces increased yields of phenoxycycloalkanol product coupled with reduced amounts of undesirable by-products relative to typically employed prior art processes.

EXAMPLES

The following Examples are intended to further illustrate the invention and are not intended to limit the scope of the invention in any manner whatsoever.

EXAMPLE 1

Fifteen grams (0.1 mole) of p-tert-butylphenol and 6.7 mg (0.29 mmole) of sodium metal were combined in a flask previously dried by sweeping with nitrogen gas. The two solids were heated to 210° C. and maintained at this temperature under agitation while 9.8 grams (0.1 mole) of liquid cyclohexene oxide were added dropwise. The cyclohexene oxide was introduced over a period of 40 minutes during which time the color of the contents of the flask changed from pale yellow to nearly colorless. The mixture was heated for an additional 30 minutes at this temperature (210° C.) to complete the reaction. The product mixture was swept with nitrogen gas and heated under reduced pressure of 10 mm Hg (1.33 kPa) to remove unreacted cyclohexene oxide. The product obtained, 2-(4-tert-butylphenoxy)cyclohexanol, crystallized upon standing. A yield of 22.8 grams, equivalent to 92% of the theoretical of the product, was obtained.

The product was subjected to gas chromatography (GC) assay. The assay indicated 82.9% 2-(4-tert-butylphenoxy)cyclohexanol; 10.1% unreacted p-tert-butylphenol; and 7.0% of 2-[2-(4-tert-butylphenoxy)cyclohexyloxy]cyclohexanol.

EXAMPLE 2

375.6 grams (2.5 moles) of p-tert-butylphenol and 0.94 gram (0.25 weight percent, based on the weight of p-tert-butylphenol) of sodium metal were introduced into a 2-liter 3-necked reaction flask, equipped with a dry-ice condenser, mechanical stirrer, thermometer, 250 ml addition funnel and nitrogen inlet tube. The flask was heated under a blanket of nitrogen gas to melt the p-tert-butylphenol. Most of the p-tert-butylphenol was melted at 95°–100° C. The sodium metal reacted rapidly with the evolution of hydrogen gas. Thereafter, the contents of the flask were further heated and maintained at a temperature of 195°–200° C. At this temperature, 265.6 ml (2.63 moles) of cyclohexene oxide were added dropwise at a rate such that no cyclohexene oxide vapor escaped through the condenser. After this addition, the reaction mixture was further heated for an additional hour. It was then cooled to 120° C. and transferred to a 1-liter, round-bottom flask. The crude product was stripped at 140° C. at a pressure of 0.1 to 1.0 mm Hg (13.3–133 Pa) to remove excess cyclohexene oxide and unreacted p-tert-butylphenol. On cooling, the product was a colorless solid present in a yield of 624.8 grams having a melting point of 86°–90° C.

A gas chromatography assay was conducted on the product. The 2-(4-tert-butylphenoxy)cyclohexanol represented 97.6% and p-tert-butylphenol represented 0.27% of the product.

EXAMPLE 3

68,200 grams (455 moles) of p-tert-butylphenol was placed in a 75-gallon stainless steel reactor, equipped with an oil heating system. The reactor was exhausted to a high vacuum and then flushed with nitrogen gas. As a result of these steps, less than 0.25% of oxygen remained in the reactor. At this point the reactor was closed and heated to between 130° and 140° C. to melt the p-tert-butylphenol. While agitating, the reactor was cooled to 104-110° C. Upon reaching this temperature, 170.25 grams of sodium metal were added. This addition occurred in three steps. During the addition, a slow stream of nitrogen gas was introduced and the reactor vented through a steam-traced pipe. After each addition of sodium, an exotherm (3 to 4° C.) was observed. Upon completion of the sodium addition, nitrogen flow was cut off and the reactor closed. The reactor was thereupon heated to a temperature of approximately 195° C. 47,670 grams (486 moles) of cyclohexene oxide were added to the reactor at a rate sufficient to maintain the temperature at about 195° C. and at a pressure of not more than 5 psig (34.5 kPa). The addition of cyclohexene oxide was completed in three hours. For an additional two hours the reaction was maintained at 195° C. Thereupon, the reaction mixture was cooled to 150° C. and stripped under a reduced pressure (7.0 mm Hg, 931 Pa) at 150° C. to remove excess cyclohexene oxide and unreacted p-tert-butylphenol.

A sample of the product was analyzed by gas chromatography. This assay resulted in the determination that the product represented 94.4% 2-(4-tert-butylphenoxy)cyclohexanol and 3.6% 2-[2-(4-tert-butylphenoxy)cyclohexyloxy]cyclohexanol by-product. No unreacted p-tert-butylphenol was discovered in the assay of the product.

EXAMPLE 4

Employing the procedure of Example 1, 75.1 grams (0.5 mole) of p-tert-butylphenol were introduced with 0.12 gram of sodium metal (0.15 weight percent, based on the weight of the p-tert-butylphenol). 53 ml (0.525 mole) of cyclohexene oxide were added to the reaction mixture. A crude product yield of 115.7 grams (93.3%) was obtained. A gas chromatography assay indicated that the product was 89.5% 2-(4-tert-butylphenoxy)cyclohexanol and 3.2% p-tert-butylphenol.

EXAMPLE 5

The procedure of Example 2 was identically repeated except that sodium methoxide was employed as the catalyst. The sodium methoxide was introduced as a 25 weight percent solution in methanol. The solution possessed a specific gravity of 0.945 and 10 ml of this solution was introduced dropwise into the flask.

A product yield of 622.3 grams was obtained. A gas chromatography assay of the product indicated that it represented 96% 2-(4-tert-butylphenoxy)cyclohexanol. The GC assay furthermore indicated the absence of unreacted p-tert-butylphenol.

EXAMPLES 6 AND 7 AND COMPARATIVE EXPERIMENTS A, B AND C

In order to compare the process of this invention with prior art processes employing sodium hydroxide or lower reaction temperatures, the following series of experiments was conducted.

To a 500 ml flask equipped with a dry-ice condenser, mechanical stirrer, thermometer, addition funnel and nitrogen inlet tube were added 94 grams (0.625 mole) of p-tert-butylphenol. As is indicated in Table I below, one of the following catalysts in the amounts listed was then added to the flask.

Metallic Sodium—0.24 gram (0.25 wt % of p-tert-butylphenol)

Sodium Methoxide—25 wt % solution in $CH_3OH$, (d=0.945) 2.5 ml

Sodium Hydroxide—0.24 gram (0.25 wt % of p-tert-butylphenol)

The mixture was heated and maintained at the reaction temperature indicated in Table I. Subsequently, 67.0 ml (0.658 mole) of cyclohexene oxide was added dropwise over a period of 2.5–3.0 hours at a rate such that no cyclohexene oxide vapor escaped through the condenser. After addition of the cyclohexene oxide was complete, the reaction was maintained at the reaction temperature for 1.5–2.0 hours.

The reaction products of the reactions conducted at 195° C. were cooled to 150° C. and transferred to a 500 ml 1-neck flask, where the product was stripped under a reduced pressure (0.2 mm and oil bath temperature at 150° C.) for 3 hours to remove any volatile materials. The solid product of glycol ether was weighed and assayed by gas chromatography analysis.

The reaction products of the reactions conducted at 135° C. were then cooled to 60° C. and transferred to a 1-neck 500 ml flask. After being left to stand about 18 hours the product was weighed and assayed by gas chromatographic analysis.

The results of the above analyses are summarized in Table I below.

TABLE I

| Example or Comparative Experiment | A | B | 6 | 7 | C |
|---|---|---|---|---|---|
| Reaction Temperature | 135° C. | 135° C. | 195° C. | 195° C. | 195° C. |
| Catalyst | Na | NaOCH$_3$ | Na | NaOCH$_3$ | NaOH |
| Analysis of Product (wt percent) | | | | | |
| Phenoxycycloalkanol | 60.5 | 51.7 | 92.2 | 93.2 | 90 |
| Diether* | 7.2 | 5.9 | 2.0 | 1.7 | 4.6 |
| Unreacted p-t-butylphenol | 20.6 | 28.4 | 0.4 | 0.6 | 1.4 |

TABLE I-continued

| Example or Comparative Experiment | A | B | 6 | 7 | C |
|---|---|---|---|---|---|
| Unreacted cyclohexene oxide** | 10.6 | 14.0 | — | — | — |

*Impurity formed by reaction of 2 molecules of cyclohexene oxide with one molecule of p-tert-butylphenol.
**This material was stripped off in runs at 195° C. before assay.

The above data indicates the increased amounts of phenoxycycloalkanol product produced—and the decreased amounts of unrecoverable diether by-product produced—by the process of this invention relative to prior art processes employing sodium hydroxide or lower reaction temperatures.

What is claimed is:

1. A process for producing a compound having the structure:

R—O—R'—OH wherein:
R is phenyl or phenyl substituted with one or more member of group consisting of:
  $C_1$–$C_4$ alkyl,
  $C_1$–$C_4$ alkoxy and methylene-dioxy; and
R' is $C_5$–$C_6$ cycloalk-1,2-ylene or $C_5$–$C_6$ cycloalk-1,2-ylene substituted with one or more member of the group consisting of:
  $C_1$–$C_4$ alkyl and
  $C_1$–$C_4$ alkoxy;
comprising reacting at between about 170° C. and about 225° C.:
(A) a compound having the formula ROH wherein R is as defined above; and
(B) at least one member of the group consisting of:
  cyclopentene oxide,
  cyclohexene oxide,
  cyclopentene oxide substituted with one or more member of the group consisting of $C_1$–$C_4$ alkyl, $C_1$–$C_4$ alkoxy and vinyl; and
  cyclohexene oxide substituted with one or more member selected from the group consisting of $C_1$–$C_4$ alkyl, $C_1$–$C_4$ alkoxy, and vinyl;
in the presence of an effective amount of sodium-containing catalyst selected from the group consisting of sodium metal, $C_1$–$C_8$ sodium alkoxide, $C_6$–$C_{10}$ sodium aryloxide, $C_7$–$C_9$ sodium alkaryloxide and sodium hydride.

2. A process in accordance with claim 1 wherein the reaction is performed at between about 170° and about 210° C.

3. A process in accordance with claim 1 wherein the amount of sodium-containing catalyst is in the range of between about 0.01% and about 5% by weight, based on the weight of component (A).

4. A process in accordance with claim 3 wherein the sodium-containing catalyst is present in a concentration of between about 0.05% and about 1% by weight, based on the weight of component (A).

5. A process in accordance with claim 1 wherein said sodium-containing catalyst is selected from the group consisting of sodium metal, sodium methoxide, sodium ethoxide, sodium isopropoxide, sodium phenoxide, sodium para-tert-butylphenoxide and sodium p-tolueneoxide.

6. A process in accordance with claim 5 wherein said sodium-containing catalyst is sodium metal.

7. A process in accordance with claim 5 wherein said sodium-containing catalyst is sodium methoxide.

8. A process in accordance with claim 5 wherein said sodium-containing catalyst is para-tert-butylphenoxide.

9. A process in accordance with claim 1 wherein component (A) is 4-tert-butylphenol and component (B) is cyclohexene oxide.

* * * * *